United States Patent [19]

Loh

[11] Patent Number: 4,534,785

[45] Date of Patent: Aug. 13, 1985

[54] HERBICIDAL 5-DEOXY-3-O-ARYLMETHYL OR SUBSTITUTED ARYLMETHYL-1,2-O-ETHYLENE-ALPHA-D-XYLOFURANOSE DERIVATIVES

[75] Inventor: William Loh, Petaluma, Calif.

[73] Assignee: Chevron Research Company, San Francisco, Calif.

[21] Appl. No.: 589,815

[22] Filed: Mar. 15, 1984

[51] Int. Cl.$^3$ .................. A01N 43/08; C07H 17/04
[52] U.S. Cl. ........................................ 71/88; 536/4.1; 536/18.1; 536/18.4
[58] Field of Search .................... 536/4.1, 18.1, 18.4; 71/88

[56] References Cited

U.S. PATENT DOCUMENTS 3,586,664  6/1971  Kohno et al. .................. 536/4.1
4,429,119  1/1984  Loh .................................... 71/88

FOREIGN PATENT DOCUMENTS 0154992  12/1980  Japan ............................ 536/4.1

Primary Examiner—Johnnie R. Brown
Attorney, Agent, or Firm—J. A. Buchanan, Jr.; L. S. Squires

[57] ABSTRACT

5-Deoxy-3-O-arylmethyl or substituted arylmethyl-1,2-O-ethylene-alpha-D-xylofuranose and 5-C-alkyl, alkylidenyl and alkenyl derivatives thereof. The compounds are useful as herbicides and plant growth regulators.

21 Claims, No Drawings

HERBICIDAL 5-DEOXY-3-O-ARYLMETHYL OR SUBSTITUTED ARYLMETHYL-1,2-O-ETHYLENE-ALPHA-D-XYLOFURANOSE DERIVATIVES

BACKGROUND OF THE INVENTION

This invention relates to 5-deoxy, 5-C-alkyl, 5-C-alkenyl and 5-C-alkylidene-5-deoxy-3-O-arylmethyl and substituted arylmethyl-1,2,-O-ethylene-alpha-D-xylofuranose derivatives and to the application of such compounds as herbicides and plant growth regulators. The invention also relates to the preparation of such compounds.

The laboratory preparation of 3-O-benzyl-5-deoxy-1,2-O-isopropylidene-alpha-D-xylofuranose for the purpose of conducting academic sugar studies is referenced in Tetrahedron Letters No. 26, pp. 2447–2448 (1979). The preparation of 3-O-benzyl-5-deoxy-1,2-O-isopropylidene-5-C-propyl-alpha-D-xylofuranose as an intermediate in the multistep synthesis of the antibiotic (—)-Canadensolide is described in Tetrahedron Letters No. 35, pp. 3233–3236 (1978) and J. Chem. Soc. Jap., Chem. Ind. Chem. 1981(5), 769–775. The laboratory preparation of 3-O-benzyl-5-deoxy-5-C-methylene-1,2-O-isopropylidene-alpha-D-xylofuranose relative to certain academic studies is described in numerous publications, including Synthesis 636 (1980); Tetrahedron Letters 4841 (1979); Carbohydrate Research 48, 143 (1976) Tetrahedron Letters 2623 (1975); Helv. Chim Acta 1303 (1973); J. Chem. Soc. Perkin Trans I. 38 (1973); Carbohyd. Research 26, 230 (1973); Carbohyd. Research 22, 227 (1972); Carbohyd. Research, 215 (1970); J. Amer. Chem. Soc. 78, 2846 (1956); Carbohyd. Res. 7, 161 (1968), Methods in Carbohyd. Chem. Vol. VI 297 (1972).

The laboratory preparation of 3-O-benzyl-5-deoxy-5-C-propylidene-1,2-O-isopropylidene-alpha-D-xylofuranose is described in Tetrahedron Letters 3233 (1978) and the laboratory preparation of 3-O-benzyl-5,6-dideoxy-1,2-O-isopropylidene-5-C-methylene-alpha-D-xylo-hexofuranose is described in Helvetica Chimica Acta 58, 1501 (1975).

The laboratory preparation of 3-O-benzyl-6,7-dideoxy-1,2-O-isopropylidene-alpha-D-xylo-heptofuranos-5-ulose and/or 3-O-benzyl-6-deoxy-1,2-O-isopropylidenealpha-D-xylo-hexofuranos-5-ulose for academic studies is described in Carbohydrate Research 31 (1973), pages 387–396; Carbohydrate Research 29 (1973), pages 11–323; Bulletin of the Chemical Society of Japan, 51 (12) (1978), pages 3595–3598; Journal of Organic Chemistry 44 (1979), pages 4294–4299; Journal of Organic Chemistry 46, (1981), pages 1296–1309; Helv. Chim. Acta 56, 1802 (1973); Carbohydrate Research 26, 441 (1973); Chem. Ber. 102, 820 (1969) and J. Org. Chem. 27, 2107 (1962).

U.S. Pat. Nos. 4,116,669, 4,146,384 and 4,330,320 and German Patent DS 2,860,975 disclose a broad range of tetrahydrofuran derivatives and attribute herbicidal activity to these derivatives. U.S. Pat. Nos. 3,919,252, 4,004,911 and 4,207,088 disclose dioxalane derivatives and dioxane derivatives and attribute grass herbicidal activity to these derivatives. The sodium salt of 2,3:4,6-bis-O-(1-methylethylidene)-O-(L-xylo-2-hexulofuranosonic acid) is sold as a pinching agent for azaleas and ornamentals and a growth retardant for shrubs, hedges and ground covers and is disclosed in U.S. Pat. No. 4,007,206.

The application of 5-C-alkyl-3-O-benzyl-1,2-O-isopropylidene alpha-D-xylo-pentodialdofuranose as herbicides and plant growth regulators is described by B. McCaskey in commonly assigned copending application Ser. No. 387,590 filed June 11, 1982.

In my copending applications Ser. No. 409,236, filed Aug. 18, 1982, now U.S. Pat. No. 4,429,119, and Ser. No. 559,126, filed Dec. 7, 1983, I disclosed certain optionally substituted 5-deoxy-3-O-arylmethyl-1,2-O-alkylidene-alpha-D-xylofuranose derivatives which are useful as herbicides and plant growth regulators.

SUMMARY OF THE INVENTION

The present invention provides compounds having herbicidal activity and plant growth regulating activity and provides method and compositions for preventing or retarding unwanted vegetation and for controlling the growth of vegetation. Certain of the active compounds are composed only of hydrogen, oxygen and carbon and hence are very desirable from an environmental standpoint because they decompose into innocuous carbon-oxygen moieties and water. I have further found that biological activity in tetrahydrofuranyl nucleolus compounds is very unpredictable. For example, even though the compounds and compositions of the present invention exhibit very good herbicide activity, especially grass pre-emergence herbicide activity, and plant growth regulating activity, a number of closely related analogs and even the 3-epimers of the present compounds fail to exhibit such activity. In general, the compounds of the invention exhibit superior pre-emergence grass herbicidal activity to their broadleaf and post-emergence herbicidal activity and a number of the compounds are selective pre-emergence grass herbicides with little or no broad-leaf phytotoxicity or post-emergence phytotoxicity.

In one aspect the invention provides compounds having the formula:

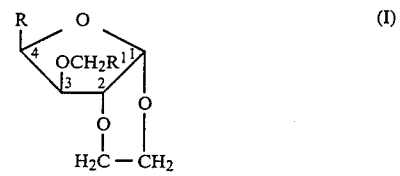

wherein
R is a linear alkyl having 1 through 4 carbon atoms or a linear alkenyl having 2 through 4 carbon atoms;
$R^1$ is 2-trifluoromethylphenyl, aryl having 6 through 10 carbon atoms, or substituted aryl having 1 through 4 substituents independently selected from the group of lower alkyl, lower alkoxy, cyano, and halo.

The compounds of Formula I are (D) optically active and can comprise various isomers. Formula (I) is intended to represent the respective pure isomers as well as mixtures thereof, having the relative orientations at C-1, 2, 3 and 4 positions shown in Formula (I), and such respective isomers and mixtures are encompassed within the invention.

The present invention provides a herbicidal composition comprising a carrier and a herbicidally effective amount of the compound(s) of formula I.

The present invention also provides a method for preventing or controlling the growth of unwanted vegetation, especially grasses, which comprises treating the growth medium and/or the foliage of such vegetation with a herbicidally effective amount of the compound of Formula I.

In another aspect, the present invention provides a plant growth regulating composition comprising a carrier and an effective amount of the plant growth regulating compound of the Formula I.

The present invention also provides a method for regulating plant growth which comprises treating the growth medium and/or the foliage of such vegetation with a plant growth regulating effective amount of the compound of Formula I.

The present invention also provides chemical intermediates and processes for preparing the compounds of Formula I, for example, the compounds of Formula I, wherein R is alkenyl, are useful as intermediates for the compounds of Formula I, wherein R is alkyl.

The invention will be further described hereinbelow.

FURTHER DESCRIPTION OF THE INVENTION AND THE PREFERRED EMBODIMENTS

Illustrations of typical compounds of Formula I of the present invention can be had by reference to Examples 4 and 5 set forth hereinbelow. In terms of substituents the preferred compounds are those wherein R is a linear alkyl, especially ethyl or propyl. The preferred $R^1$ substituent is aryl and monosubstituted aryl preferably having a single substituent selected from the group lower alkyl, lower alkoxy, and halo. More preferably, $R^1$ is phenyl or 2-substituted phenyl especially phenyl, 2-methylphenyl or 2-halophenyl, especially 2-fluorophenyl and 2-chlorophenyl.

The compounds of Formula I can be conveniently prepared via the following schematically represented process:

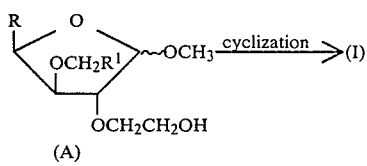

wherein R and $R^1$ are as defined hereinabove.

This reaction can be effected by contacting compound A with a suitable cyclizing agent (e.g., hydrochloric acid) preferably in an inert organic solvent.

Typically, this reaction is conducted at temperatures in the range of about from 0° to 100° C., preferably 15° to 50° C., for about from 1 to 50 hours, preferably 12 to 24 hours, using about from 0.001 to 0.1 mole equivalents, preferably 0.01 to 0.05 mole equivalents of the cyclizing agent per mole of compound A. Suitable cyclizing agents which can be used include, for example, hydrochloric acid, sulfuric acid, toluenesulfonic acid, benzenesulfonic acid, camphorsulfonic acid, and the like. Suitable inert organic solvents which can be used include, for example, chloroform, methylene chloride, carbon tetrachloride, benzene, toluene, xylene, and the like and compatible mixtures thereof.

Compound (A) can be prepared according to the following schematically represented overall reaction process sequence:

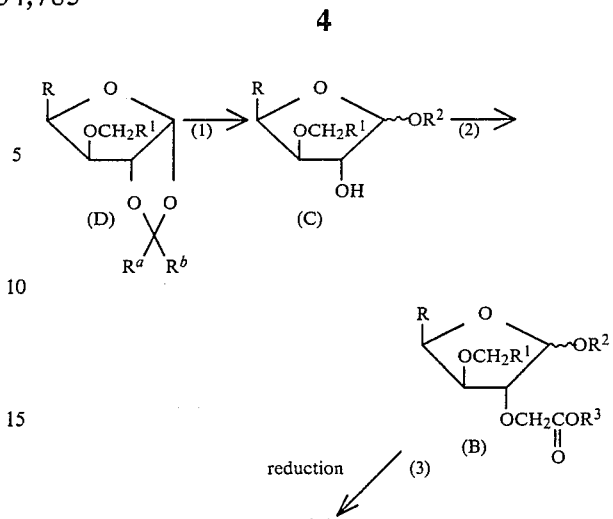

wherein R and $R^1$ are as defined hereinabove, $R^a$, $R^b$ and $R^2$ are independently lower alkyl, preferably methyl and $R^3$ is lower alkyl, preferably methyl or ethyl.

Step 1 can be effected by cleaving the 1,2-O-isopropylene group from compound D and selectively etherifying the 1-position hydroxy with an alkanol, preferably in an organic solvent. This can be effected as two steps but can also be conveniently conducted as a single process step by using excess alkanol as solvent and then bubbling hydrogen chloride through the reaction mixture. This process is typically conducted at temperatures in the range of about from 0 to 100, preferably 15 to 80, for about from 1 to 40 hours, preferably 1 to 5 hours. Typically about from 0.001 to 0.1 mole equivalents, preferably 0.01 to 0.05 mole equivalents of acid and 1 to 10 moles of alkanol are used per mole of compound D. Also where the alkanol is used as solvent a greater excess is used.

Suitable acids which can be used include, for example, hydrochloric acid, sulfonic acid, benzenesulfonic acid, toluenesulfonic acid, and the like. Also in place of, or along with, excess alkanol, the following could also be used as solvent. Generally, it is preferred to use methanol as the alkanol, because it yields the 1-methoxy (1-O-methyl) compound which gives very good results in the subsequent reactions. The starting materials of Formula D can be prepared according to the procedures described in my U.S. Pat. No. 4,429,119 and my copending application, Ser. No. 559,126, filed Dec. 7, 1983, which descriptions are hereby incorporated by reference.

Step 2 can be effected via any suitable etherification procedure, such as for example, Williamson type synthesis. Conveniently this can be effected by contacting compound C with a suitable base, thus yielding the 2-cation salt, followed by the appropriate alkyl haloacetate ester. Preferably, both steps of this reaction are conducted in an inert organic solvent. The second step is preferably conducted in the presence of a suitable catalyst and is conveniently conducted in situ with the first step of this reaction.

Typically, the first step of this reaction is conducted at temperatures in the range of about from 0° to 100° C., preferably 0° to 65° C., for about from 0.5 to 12 hours, preferably 0.5 to 1 hour using about from 1.0 to 2.0 moles, preferably 1.0 to 1.1 moles of base per mole of compound C.

The second step is typically conducted at temperatures in the range of about from 0° to 100° C., preferably 25° to 75° C., for about from 1 to 48 hours, preferably 3 to 12 hours using about from 1 to 2 moles, preferably 1.0 to 1.2 moles of alkyl haloacetate ester per mole of compound C. Typically, the second step of this reaction is conducted in situ with the first step of the reaction. Suitable inert organic solvents which can be used include, for example, tetrahydrofuran, ethyl ether, xylene, toluene, and the like and compatible mixtures thereof. Preferably, the alkyl haloacetate ester is an alkyl bromoacetate or alkyl chloroacetate. Good results can be obtained using methyl or ethyl bromoacetate. Suitable bases which can be used include, for example, sodium hydride, potassium hydride, sodium hydroxide, butyl lithium, and the like. Suitable catalysts which can be used for the second step include, for example, tetrabutyl ammonium iodide; tetrabutylammonium bromide, benzyltriethylammonium chloride, tricaprylylmethylammonium chloride, and the like.

The third step can be effected by any suitable procedure capable of reducing the alkyl carboxy ester group to an alcohol (i.e., —CH$_2$OH). This can be conveniently effected by contacting compound B with a hydride reducing agent, preferably in an inert organic solvent.

Typically, this reduction is conducted at temperatures in the range of about from 0° to 100° C., preferably 0 to the boiling point of the solvent, for about from 0.5 to 48 hours, preferably 1 to 5 hours, using about from 1 to 10 moles, preferably 1 to 5 moles of reducing hydride per mole of compound C.

Suitable reducing hydrides which can be used include, for example, lithium, aluminum hydride; sodium borohydride; lithium borohydride, and the like. Suitable inert organic solvents which can be used include, for example, tetrahydrofuran; diethyl ether; dibutyl ether, diglyme; glyme; dioxane, and the like and mixtures thereof.

General Process Applications

In the above-described processes, it is generally preferable to separate the respective products before proceeding with the next step in the reaction sequence unless expressly stated otherwise. These products can be recovered from their respective reaction product mixtures by any suitable separation and purification procedure, such as, for example, recrystallization and chromatography. Suitable separation and purification procedures are, for example, illustrated in the Examples set forth hereinbelow. Also generally it is preferred to use the appropriate isomer starting material having the same orientation as Compound I. However, isomer mixtures of starting materials can also be used. In this case the product will be a mixture of Compound I and its isomers. Compound I can then be separated from the isomer mixture or applied as a mixture.

Generally, the reactions described above are conducted as liquid phase reaction and hence pressure is generally not significant except as it affects temperature (boiling point) where reactions are conducted at reflux. Therefore, these reactions are generally conducted pressures of from 300 to 3000 mm of mercury and conveniently are conducted at about atmospheric or ambient pressure. In the case of the hydrogenation described above, the hydrogenation is typically conducted by bubbling hydrogen through the substrate, dissolved in a solvent, or placing the substrate solution under hydrogen. Thus, the hydrogenation is typically conducted under a modest pressure, typically about from 800 to 3000 mm Hg.

It should also be appreciated that where typical or preferred process conditions (e.g., reaction temperatures, times, mol ratios of reactants, solvents, etc.) have been given, that other process conditions could also be used, although typically with poor yields or economies. Optimum reaction conditons (e.g., temperature, reaction time, mol ratios, solvents, etc.) may vary with the particular reagents or organic solvents used but can be determined by routine optimization procedures.

Where optical isomer mixtures are obtained, the respective optical isomers can be obtained by conventional resolution procedures, for example, by converting the isomer mixture to an acid derivative and reacting with an optically active base which will yield a mixture of optical salts, of the desired compound, which can be resolved by conventional procedures (e.g., crystallization) into the respective plus and minus optical salts.

Definitions

As used herein the following terms have the following meanings unless expressly stated to the contrary:

The term "lower alkyl" refers to straight- and branched-chain alkyl groups having a total of from 1 through 4 carbon atoms and includes primary, secondary and tertiary alkyl groups. Typical lower alkyls include, for example, methyl, ethyl, n-propyl, isopropyl, n-butyl, t-butyl. The term "linear alkyl" refers to straight-chain alkyl groups. The term linear alkyl having 1 through 4 carbon atoms refers to the group of methyl, ethyl, propyl and butyl.

The term "lower alkenyl" refers to alkenyl groups having 2 through 4 carbon atoms and includes for example vinyl; 1-propenyl, 2-propenyl, 1-butenyl, 2-methyl-prop-1-enyl and the like. The term "linear alkenyl" refers to straight-chained alkenyl groups.

The term "halo" refers to the group of fluoro, chloro, bromo and iodo.

The term "aryl" refers to aryl groups having 6 through 10 carbon atoms and includes, for example, phenyl, naphthyl, indenyl, and the like.

The term "substituted aryl" refers to aryl groups having 1 or 2 substituents independently selected from the grup of lower alkyl, lower alkoxy and halo. Typical substituted aryl includes, for example, 2-fluorophenyl, 2-chlorophenyl, 2,6-dimethylphenyl, 2-methylphenyl, 2,4-dimethylphenyl, 2,5-dimethylphenyl, 2,4-dichlorophenyl, 2-methoxyphenyl and the like.

The term "arylalkyl" refers to the groups —CH$_2$Ar; —CH$_2$CH$_2$Ar and —CH(CH$_3$)Ar wherein Ar is aryl.

The term "substituted arylalkyl" or "ring substituted arylalkyl" refers to the groups —CH$_2$Ar'; —CH$_2$CH$_2$Ar' and —CH(CH$_3$)Ar' wherein Ar' is substituted aryl.

As exemplary of the sugar nomenclature used herein the term "3-O-benzyl-1,2-O-ethylene-5-deoxy-5-C-methyl-alpha-D-xylofuranose" refers to the compound having the following structural formula:

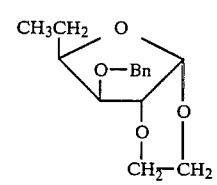

wherein Bn is benzyl.

Utility

The compounds of Formula I exhibit very good pre-emergence against grasses and also in some cases exhibit modest pre-emergence activity against broad-leaf plants and weak to good post-emergence herbicidal activity. Further, by proper reduction of the dosage, the compounds can be safely applied as selective pre-emergence grass herbicides to prevent or reduce the growth of grasses amongst broad leaf crops such as soybean. The preferred herbicidal compounds of Formula I are those wherein R is ethyl or propyl and especially the compound wherein R is ethyl.

Generally, for post-emergent applications, the herbicidal compounds are applied directly to the foliage or other plant parts. For pre-emergence applications, the herbicidal compounds are applied to the growing medium, or prospective growing medium, of the plant. The optimum amount of the herbicidal compound or composition will vary with the particular plant species, and the extent of part plant growth and the particular part of the plant which is contacted. The optimum dosage will also vary with the general location, or environment, of application (e.g., sheltered areas such as greenhouses compared to exposed areas such as fields), and type and degree of control desired. Generally, for both pre- and post-emergent control, the present compounds are applied at rates of about from 0.2 to 60 kg/ha, preferably about from 0.5 to 10 kg/ha.

Also, although in theory the compounds can be applied undiluted, in actual practice they are generally applied as a composition or formulation comprising an effective amount of the compound(s) and an acceptable carrier. An acceptable carrier (agriculturally acceptable carrier) is one which does not significantly adversely affect the desired biological effect achieved by the active compounds, save to dilute it. Typically, the composition contains about from 0.05 to 95% by weight of the compound of Formula (I) or mixtures thereof. Concentrates can also be made having higher concentrations designed for dilution prior to application. The carrier can be a solid, liquid, or aerosol. The actual compositions can take the form of granules, powders, dusts, solutions emulsions, slurries, aerosols, and the like.

Suitable solid carriers which can be used include, for example, natural clays (such as kaolin, attapulgite, montmorillonite, etc.), talcs, pyrophyllite, diatoamaceous silica, synthetic fine silica, calcium aluminosilicate, tricalcium phosphate, and the like. Also, organic materials, such as, for example, walnut shell flour, cotton-seed hulls, wheat flour, wood flour, wood bark flour, and the like can also be used as carriers. Suitable liquid diluents which can be used include, for example, water, organic solvents (e.g., hydrocarbons such as benzene, toluene, dimethylsulfoxide, kerosene, diesel fuel, fuel oil, petroleum naphtha, etc.), and the like. Suitable aerosol carriers which can be used include conventional aerosol carriers such as halogenated alkanes, etc.

The composition can also contain various promoters and surface-active agents which enhance the rate of transport of the active compound into the plant tissue such as, for example, organic solvents, wetting agents and oils, and in the case of compositions designed for pre-emergence application agents which reduce the leachability of the compound.

The composition can also contain various compatible adjuvants, stabilizers, conditioners, insecticides, fungicides, and if desired, other herbicidally active compounds.

The compounds of the present invention also exhibit plant growth regulating activity and especially root growth inhibition; foliage regrowth inhibition and crop enhancement. The former activity is useful where top growth is desirable. Foliage regrowth inhibition is desirable in cases such as the harvesting of cotton. In harvesting cotton, defoliants and desiccants are frequently used to remove the leaves of the cotton plant thus making the cotton more accessible. In such cases regrowth inhibitors are useful to inhibit the regrowth of leaves, before harvesting is completed. Crop enhancement is produced by pinching and increasing crop bearing branching in crops such as soy bean.

The present compounds of Formula I can be applied in pure form, but more pregmatically, as in the case of herbicide application, are applied in combination with a carrier. The same types of carriers as set forth hereinabove with respect to the herbicide compositions can also be used. Depending on the desired application, the plant growth regulating composition can also contain, or be applied in combination with other compatible ingredients such as desiccants, defoliants, surface-active agents, adjuvants, fungicides, insecticides and selective herbicides. Typically, the plant growth regulating composition will contain a total of about from 0.005 to 90 wt. %, of the compound(s) of Formula (I) depending on whether the composition is intended to be applied directly or diluted first.

A further understanding of the invention can be had in the following non-limiting Preparation and Examples. Wherein, unless expressly stated to the contrary, all temperatures and temperature ranges refer to the Centigrade system and the term "ambient" or "room temperature" refers to about 20°–25° C. The term "percent" or "%" refers to weight percent and the term "mole" or "moles" refers to gram moles. The term "equivalent" refers to a quantity of reagent equal in moles, to the moles of the preceding or succeeding reactant recited in that example in terms of finite moles or finite weight or volume. Also where necessary examples are repeated to provide additional starting material for subsequent examples.

EXAMPLE 1

Methyl
3-O-(2-chlorobenzyl)-5-deoxy-5-C-methyl-alpha,beta-D-xylofuranoside

In this example a solution containing 20 g of 3-O-(2-chlorobenzyl)-1,2-O-isopropylidene-5-deoxy-5-C-methyl-alpha-D-xylofuranose in 300 ml of methanol was heated to reflux. Gaseous hydrogen chloride was then bubbled into the refluxing solution for about 3 to 5 minutes. The solution was then refluxed for another 2 hours and then cooled and concentrated by evaporation. The concentrate was mixed with ethyl ether and water and extracted. The ether extract was washed with saturated aqueous sodium carbonate followed by water until neutral and then dried over anhydrous magnesium sulfate and concentrated affording 17.4 g of the title product as a mixture of the alpha and beta glycoside anomers.

EXAMPLE 2

Methyl 3-O-(2-chlorobenzyl)-2-O-(ethoxycarbonylmethyl)-5-deoxy-5-C-methylalpha, beta-D-xylofuranoside In this example 2.9 g (0.06 mole) or 50 wt % of sodium hydride was added portionwise to 14.3 g (50 mmole) of methyl 3-O-(2-chlorobenzyl)-5-deoxy-5-C-methyl-alpha, beta-D-xylofuranoside dissolved in 100 ml of tetrahydrofuran, at room temperature, under a nitrogen atmosphere. The solution was cooled to about 0° C. and then 0.3 g of tetrabutylammonium iodide was added, followed by the dropwise addition of 9.2 g (55 mmole) of ethyl bromoacetate. The mixture was then stirred overnight (about 14–16 hours) at room temperature and then concentrated by evaporation under reduced pressure. The concentrate was mixed with ethyl ether and washed with water until neutral and then dried over anhydrous magnesium sulfate and concentrated by evaporation. The residue was dissolved in 100 ml of acetonitrile, washed twice with small amounts of hexane to remove mineral oil and then concentrated by evaporation affording B 15.6 g of liquid product determined to be a mixture of the alpha and beta isomers of the title compound. The product was purified by flash chromatography employing tethydrofuran-hexane as eluant.

EXAMPLE 3

Methyl 3-O-(2-chlorobenzyl)-2-O-(2-hydroxyethyl)-5-deoxy-5-C-methyl-alpha, beta-D-xylofuranoside In this example 0.53 g of lithium aluminum hydride was slowly added to a solution containing 5.2 g of methyl 3-O-(2-chlorobenzyl)-2-O-(ethoxycarbonylmethyl)-5-deoxy-5-C-methyl-alpha, beta-D-xylofuranoside in 100 ml of tetrahydrofuran at about 0° C. The mixture was then allowed to raise to room temperature and stirred at this temperature for 2 hours. Five ml of ethyl acetate was then added followed by the successive addition of 1 ml of water, 1 ml of 15 wt % aqueous sodium hydroxide and 3 ml of water. The mixture was then filtered and the filter cake washed with ethyl ether. The filtrate and ether washings were combined and evaporated under reduced pressure. The resulting residue was mixed with ethyl ether and then washed with water and evaporated down to 4.8 g of a mixture of the alpha and beta glycosides of the title compound as a colorless liquid.

EXAMPLE 4

3-O-(2-Chlorobenzyl)-1,2-O-ethylene-5-deoxy-5-C-methyl-alpha-D-xylofuranose

In this example about 4.8 g of a crude methyl 3-O-(2-chlorobenzyl)-2-O-(2-hydroxyethyl)-5-deoxy-5-C-methyl-alpha, beta-D-glucofuranoside was dissolved in 100 ml of chloroform at room temperature. Gaseous hydrogen chloride was bubbled into the solution for 1 or 2 minutes. The mixture was then stirred at room temperature for 40 hours. The mixture was then mixed with aqueous saturated sodium bicarbonate solution and washed with water until neutral. The mixture was then dried over anhydrous magnesium sulfate, and then evaporated affording 3.8 g of the title compound as a yellow liquid.

Similarly by following the same procedure but using the corresponding 2-O-(2-hydroxymethyl) alpha and/or beta D-xylofuranoside derivatives as starting materials the following compounds can be prepared. (The 2-O-(2-hydroxymethyl)-alpha and/or beta D-xylofuranoside derivatives can be prepared by applying the procedures of Examples 1–3 starting with the corresponding 1,2-O-isopropylidene-alpha-D-xylofuranose derivative in Example 1):

3-O-(2-chlorobenzyl)-1,2-O-ethylene-5-deoxy-alpha-D-xylofuranose;

3-O-(2-chlorobenzyl)-1,2-O-ethylene-5-deoxy-5-C-ethyl-alpha-D-xylofuranose;

3-O-(2-chlorobenzyl)-1,2-O-ethylene-5-deoxy-5-C-propyl-alpha-D-xylofuranose;

3-O-(2-chlorobenzyl)-1,2-O-ethylene-5-deoxy-5-C-methylene-alpha-D-xylofuranose (i.e., R=vinyl);

3-O-(2-chlorobenzyl)-1,2-O-ethylene-5-deoxy-5-C-vinyl-alpha-D-xylofuranose (i.e., R=allyl);

3-O-(2-fluorobenzyl)-1,2-O-ethylene-5-deoxy-5-C-methyl-alpha-D-xylofuranose;

3-O-(2-fluorobenzyl)-1,2-O-ethylene-5-deoxy-alpha-D-xylofuranose;

3-O-(2-fluorobenzyl)-1,2-O-ethylene-5-deoxy-5-C-ethyl-alpha-D-xylofuranose;

3-O-(2-fluorobenzyl)-1,2-O-ethylene-5-deoxy-5-C-propyl-alpha-D-xylofuranose;

3-O-(2-fluorobenzyl)-1,2-O-ethylene-5-deoxy-5-C-methylene-alpha-D-xylofuranose (i.e., R=vinyl);

3-O-(2-fluorobenzyl)-1,2-O-ethylene-5-deoxy-5-C-vinyl-alpha-D-xylofuranose (i.e., R=allyl);

3-O-benzyl-1,2-O-ethylene-5-deoxy-5-C-methyl-alpha-D-xylofuranose;

3-O-benzyl-1,2-O-ethylene-5-deoxy-alpha-D-xylofuranose;

3-O-benzyl-1,2-O-ethylene-5-deoxy-5-C-ethyl-alpha-D-xylofuranose;

3-O-benzyl-1,2-O-ethylene-5-deoxy-5-C-propyl-alpha-D-xylofuranose;

3-O-benzyl-1,2-O-ethylene-5-deoxy-5-C-methylene-alpha-D-xylofuranose (i.e., R=vinyl);

3-O-benzyl-1,2-O-ethylene-5-deoxy-5-C-vinyl-alpha-D-xylofuranose (i.e., R=allyl);

3-O-(3-methoxybenzyl)-1,2-O-ethylene-5-deoxy-5-C-methyl-alpha-D-xylofuranose;

3-O-(3-methoxybenzyl)-1,2-O-ethylene-5-deoxy-alpha-D-xylofuranose;

3-O-(3-methoxybenzyl)-1,2-O-ethylene-5-deoxy-5-C-ethyl-alpha-D-xylofuranose;

3-O-(3-methoxybenzyl)-1,2-O-ethylene-5-deoxy-5,5-C-dimethyl-alpha-D-xylofuranose;

3-O-(3-methoxybenzyl)-1,2-O-ethylene-B 5-deoxy-5-C-propyl-alpha-D-xylofuranose;

3-O-(3-methoxybenzyl)-1,2-O-ethylene-5-deoxy-5-C-methylene-alpha-D-xylofuranose (i.e., R=vinyl);

3-O-(3-methoxybenzyl)-1,2-O-ethylene-5-deoxy-5-C-vinyl-alpha-D-xylofuranose (i.e., R=allyl);

3-O-(2,6-dimethylbenzyl)-1,2-O-ethylene-5-deoxy-5-C-methyl-alpha-D-xylofuranose;

3-O-(2,6-dimethylbenzyl)-1,2-O-ethylene-5-deoxy-alpha-D-xylofuranose;

3-O-(2,6-dimethylbenzyl)-1,2-O-ethylene-5-deoxy-5-C-ethyl-alpha-D-xylofuranose;

3-O-(2,6-dimethylbenzyl)-1,2-O-ethylene-5-deoxy-5-C-propyl-alpha-D-xylofuranose;

3-O-(2,6-dimethylbenzyl)-1,2-O-ethylene-5-deoxy-5-C-methylene-alpha-D-xylofuranose (i.e., R=vinyl);

3-O-(2,6-dimethylbenzyl)-1,2-O-ethylene-5-deoxy-5-C-vinyl-alpha-D-xylofuranose (i.e., R=allyl);

3-O-(2-naphthamethyl)-1,2-O-ethylene-5-deoxy-5-C-methyl-alpha-D-xylofuranose;
3-O-(2-naphthamethyl)-1,2-O-ethylene-5-deoxy-alpha-D-xylofuranose;
3-O-(2-naphthamethyl)-1,2-O-ethylene-5-deoxy-5-C-ethyl-alpha-D-xylofuranose;
3-O-(2-naphthamethyl)-1,2-O-ethylene-5-deoxy-5-C-propyl-alpha-D-xylofuranose;
3-O-(2-naphthamethyl)-1,2-O-ethylene-5-deoxy-5-C-methylene-alpha-D-xylofuranose (i.e., R=vinyl);
3-O-(2-naphthamethyl)-1,2-O-ethylene-5-deoxy-5-C-vinyl-alpha-D-xylofuranose (i.e., R=allyl).
3-O-(2-indenylmethyl)-1,2-O-ethylene-5-deoxy-5-C-methyl-alpha-D-xylofuranose;
3-O-(2-indenylmethyl)-1,2-O-ethylene-5-deoxy-alpha-D-xylofuranose;
3-O-(2-indenylmethyl)-1,2-O-ethylene-5-deoxy-5-C-ethyl-alpha-D-xylofuranose;
3-O-(2-indenylmethyl)-1,2-O-ethylene-5-deoxy-5-C-propyl-alpha-D-xylofuranose;
3-O-(2-indenylmethyl)-1,2-O-ethylene-5-deoxy-5-C-methylene-alpha-D-xylofuranose (i.e., R=vinyl);
3-O-(2-indenylmethyl)-1,2-O-ethylene-5-deoxy-5-C-vinyl-alpha-D-xylofuranose (i.e., R=allyl);
3-O-(8-chloronapth-2-ylmethyl)-1,2-O-ethylene-5-deoxy-5-C-methyl-alpha-D-xylofuranose;
3-O-(8-chloronapth-2-ylmethyl)-1,2-O-ethylene-5-deoxy-alpha-D-xylofuranose;
3-O-(8-chloronapth-2-ylmethyl)-1,2-O-ethylene-5-deoxy-5-C-ethyl-alpha-D-xylofuranose;
3-O-(8-chloronapth-2-ylmethyl)-1,2-O-ethylene-5-deoxy-5-C-propyl-alpha-D-xylofuranose;
3-O-(8-chloronapth-2-ylmethyl)-1,2-O-ethylene-5-deoxy-5-C-methylene-alpha-D-xylofuranose (i.e., R=vinyl);
3-O-(8-chloronapth-2-ylmethyl)-1,2-O-ethylene-5-deoxy-5-C-vinyl-alpha-D-xylofuranose (i.e., R=allyl);
3-O-(7-methoxynapth-2-ylmethyl)-1,2-O-ethylene-5-deoxy-5-C-methyl-alpha-D-xylofuranose;
3-O-(7-methoxynapth-2-ylmethyl)-1,2-O-ethylene-5-deoxy-alpha-D-xylofuranose;
3-O-(7-methoxynapth-2-ylmethyl)-1,2-O-ethylene-5-deoxy-5-C-ethyl-alpha-D-xylofuranose;
3-O-(7-methoxynapth-2-ylmethyl)-1,2-O-ethylene-5-deoxy-5-C-propyl-alpha-D-xylofuranose;
3-O-(7-methoxynapth-2-ylmethyl)-1,2-O-ethylene-5-deoxy-5-C-methylene-alpha-D-xylofuranose (i.e., R=vinyl);
3-O-(7-methoxynapth-2-ylmethyl)-1,2-O-ethylene-5-deoxy-5-C-vinyl-alpha-D-xylofuranose (i.e., R=allyl);
3-O-(3,6-dimethylnapth-2-ylmethyl)-1,2-O-ethylene-5-deoxy-5-C-methyl-alpha-D-xylofuranose;
3-O-(3,6-dimethylnapth-2-ylmethyl)-1,2-O-ethylene-5-deoxy-alpha-D-xylofuranose;
3-O-(3,6-dimethylnapth-2-ylmethyl)-1,2-O-ethylene-5-deoxy-5-C-ethyl-alpha-D-xylofuranose;
3-O-(3,6-dimethylnapth-2-ylmethyl)-1,2-O-ethylene-5-deoxy-5-C-propyl-alpha-D-xylofuranose;
3-O-(3,6-dimethylnapth-2-ylmethyl)-1,2-O-ethylene-5-deoxy-5-C-methylene-alpha-D-xylofuranose (i.e., R=vinyl); and
3-O-(3,6-dimethylnapth-2-ylmethyl)-1,2-O-ethylene-5-deoxy-5-C-vinyl-alpha-D-xylofuranose (i.e., R=allyl).

EXAMPLE 5

By applying the procedures described in the above Examples 1-4 using the appropriate starting materials, the compounds listed in Table A hereinbelow were prepared.

TABLE A

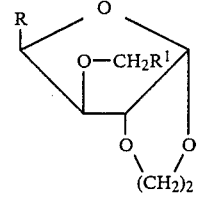
(I)

| No. | R | $R^1$ | Carbon Calc. | Carbon Found | Hydrogen Calc. | Hydrogen Found | Melting Point °C. |
|---|---|---|---|---|---|---|---|
| 1 | —$CH_2CH_3$ | $\phi$* | 68.16 | 68.11 | 7.63 | 8.49 | liquid |
| 2 | —$CH_2CH_3$ | 2-$CH_3$—$\phi$ | 69.04 | 69.06 | 7.97 | 8.20 | 63–65 |
| 3 | —$CH_2CH_3$ | 2-Cl—$\phi$ | 60.30 | 59.10 | 6.41 | 6.91 | liquid |

*$\phi$ = phenyl

EXAMPLE 6

In this example, the compounds of Table A were respectively tested for pre-emergent and post-emergent activity against a variety of grasses and broad-leaf plants including one grain crop and one broad-leaf crop. The compounds tested are identified in Tables A hereinabove.

Pre-Emergent Herbicide Test

Pre-emergence herbicidal activity was determined in the following manner.

Test solutions of the respective compounds were prepared as follows:

355.5 mg of test compound was dissolved in 15 ml of acetone. 2 ml of acetone containing 110 mg of a nonionic surfactant was added to the solution. 12 ml of this stock solution was then added to 47.7 ml of water which contained the same nonionic surfactant at a concentration of 625 mg/l.

Seeds of the test vegetation were planted in a pot of soil and the test solution was sprayed uniformly onto the soil surface at a dose of 15.6 micrograms/cm². The pot was watered and placed in a greenhouse. The pot was watered intermittently and observed for seedling emergence, health of emerging seedlings, etc., for a 3-week period. At the end of this period, the herbicidal effectiveness of the compound was rated based on the physiological observations. A 0- to 100-scale was used, 0 representing no phytotoxicity, 100 representing complete kill. The results of these tests are summarized in Table 1.

Post-Emergent Herbicidal Test

The test compound was formulated in the same manner as described above for the pre-emergent test. This formulation was uniformly sprayed on 2 similar pots containing plants 2 to 3 inches tall (except wild oats, soybean and watergrass which were 3 to 4 inches tall) (approximately 15 to 25 plants per pot) at a dose of 15.6 micrograms/cm², as indicated in Table 1 hereinbelow. After the plants had dried, they were placed in a greenhouse and then watered intermittently at their bases as needed. The plants were observed periodically for phytotoxic effects and physiological and morphological responses to the treatment. After 3 weeks, the herbicidal effectiveness of the compound was rated based on these observations. A 0- to 100-scale was used, 0 representing no phytotoxicity, 100 representing com-plete kill. The results of these tests are summarized in Table 2.

TABLE 1

Pre-Emergence Herbicidal Activity
Dosage rate 15.6 micrograms/cm², unless otherwise indicated.

| Compound No. | Broad-Leaf Plants % Phytotoxicity | | | | Grasses % Phytotoxicity | | | |
|---|---|---|---|---|---|---|---|---|
| | Lambs Quarter | Mustard | Pigweed | Soybean | Crab Grass | Water Grass | Wild Oats | Rice |
| 1 | 95 | 100 | 40 | 0 | 100 | 100 | 90 | 95 |
| 2 | 90 | 40 | 90 | 60 | 100 | 95 | 90 | 95 |
| 3 | 30 | 0 | 0 | 0 | 100 | 100 | 70 | 100 |

TABLE 2

Post-Emergence Herbicidal Activity
Dosage rate: 15.6 micrograms/cm², unless otherwise indicated

| Compound No. | Broad-Leaf Plants % Phytotoxicity | | | | Grasses % Phytotoxicity | | | |
|---|---|---|---|---|---|---|---|---|
| | Lambs Quarter | Mustard | Pigweed | Soybean | Crab Grass | Water Grass | Wild Oats | Rice |
| 1 | 0 | 0 | 0 | 0 | 60 | 30 | 30 | 95 |
| 2 | 70 | 50 | 80 | 90 | 0 | 40 | 20 | 20 |
| 3 | 20 | 0 | 30 | 0 | 0 | 0 | 0 | 0 |

As can be seen from Tables 1 and 2, at the dosage tested the compositions of the present invention exhibited very good pre-emergence herbicide activity against grasses. Compounds Nos. 1 and 2 also exhibited good pre-emergence activity against broad-leaf plants whereas compound No. 3 was selective to grasses. Also, interestingly compound No. 1 although active against broad-leaf plants was safe with respect to soybeans. Compounds Nos. 1 and 2 also exhibited modest to good post-emergence herbicide activity against grasses and in the case of compound No. 2 also against broad-leaf plants.

Obviously, many modifications and variations of the invention described hereinabove and below in the claims can be made without departing from the essence and scope thereof.

What is claimed is:
1. A compound having the formula:

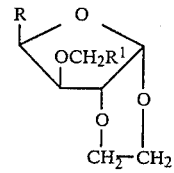

(I)

wherein
R is linear lower alkyl having 1 through 4 carbon atoms or linear alkenyl having 2 through 4 carbon atoms;
R¹ is 2-trifluoromethylphenyl, aryl having 6 through 10 carbon atoms or substituted aryl having 1 through 4 substituents independently selected from the group of lower alkyl having 1 through 4 carbon atoms, lower alkoxy having 1 through 4 carbon atoms, cyano and halo.
2. The compound of claim 1 wherein R¹ is aryl or monosubstituted aryl having a sole substituent selected from the group of lower alkyl, lower alkoxy, and halo.
3. The compound of claim 2 wherein R¹ is phenyl or monosubstituted phenyl.
4. The compound of claim 2 wherein R¹ is phenyl or monosubstituted phenyl having its sole substituent at the 2 position.
5. The compound of claim 4 wherein R is linear lower alkyl.
6. The compound of claim 5 wherein R is ethyl or propyl and R¹ is phenyl, 2-chlorophenyl, or 2-fluorophenyl or 2-methylphenyl.
7. The compound of claim 1 wherein R is lower alkyl.
8. The compound of claim 7 wherein R is ethyl or propyl.
9. The compound of claim 2 wherein R is linear lower alkyl.
10. The compound of claim 1 wherein R is linear alkenyl having 2 through 4 carbon atoms.
11. The compound of claim 1 wherein R is ethyl and R¹ is 2-chlorophenyl.
12. The compound of claim 1 wherein R is ethyl and R¹ is 2-fluorophenyl.
13. The compound of claim 1 wherein R is ethyl and R¹ is phenyl.
14. The compound of claim 13 wherein R is ethyl and R¹ is 2-methylphenyl.
15. An herbicidal composition comprising an herbicidally effective amount of the compound of claim 1, or mixtures thereof, and a compatible carrier.
16. The composition of claim 15 wherein said composition contains an amount of said compound of claim 1 or mixtures thereof effective when applied to the growth medium of grasses to prevent or reduce the germination or early growth of grasses.
17. A method for controlling undesired vegetation which comprises supplying a herbicidally effective amount of the compound of claim 1 or mixtures thereof, to the foliage or growth medium of said vegetation.
18. The method of claim 17, wherein said vegetation is grass.
19. The method of claim 18, wherein an amount of said compound of claim 1 and mixtures thereof effective to reduce or prevent the germination or early growth of grasses is applied to the growth medium of said grasses.
20. A plant growth regulating composition comprising a compatible carrier and a plant growth regulating effective amount of the compound of claim 1 or mixtures thereof.
21. A method for advantageously altering the growth pattern of plants which comprises contacting the seeds or foliage of such plants with a plant growth regulating effective amount of a compound according to claim 1 or mixtures thereof.

* * * * *